(12) United States Patent
Bayer

(10) Patent No.: US 12,109,109 B2
(45) Date of Patent: *Oct. 8, 2024

(54) INJECTOR FOR INTRAOCULAR LENSES

(71) Applicant: OPHTHALMO PRO GMBH, Sankt Ingbert (DE)

(72) Inventor: Alexander Bayer, Düsseldorf (DE)

(73) Assignee: OPHTHALMO PRO GMBH, Sankt Ingbertd (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/024,350

(22) PCT Filed: Sep. 4, 2020

(86) PCT No.: PCT/EP2020/074761
§ 371 (c)(1),
(2) Date: Nov. 7, 2023

(87) PCT Pub. No.: WO2022/048766
PCT Pub. Date: Mar. 10, 2022

(65) Prior Publication Data
US 2024/0261087 A1    Aug. 8, 2024

(51) Int. Cl.
*A61F 2/16* (2006.01)
(52) U.S. Cl.
CPC .......... *A61F 2/1672* (2013.01); *A61F 2/1667* (2013.01); *A61F 2/167* (2013.01)
(58) Field of Classification Search
CPC ........ A61F 2/16; A61F 2/1672; A61F 2/1662; A61F 2/1667; A61F 2/167; A61F 2/1675; A61F 2/1678; A61F 2/1691
See application file for complete search history.

(56) References Cited

U.S. PATENT DOCUMENTS 4,810,249 A    3/1989  Haber
6,106,496 A  *  8/2000  Arnissolle ....... A61M 25/10182
                                                          604/207
(Continued)

FOREIGN PATENT DOCUMENTS

CN    202021009293 U    6/2020
CN    202010500344 A    12/2021
(Continued)

*Primary Examiner* — Vi X Nguyen
(74) *Attorney, Agent, or Firm* — DINSMORE & SHOHL LLP

(57) ABSTRACT

An intraocular lens implantation injector has a base body and elongated actuation element projecting into a base body rear section and movably guided along an actuation axis. Actuation element movement is generated selectively by axial push actuation or by screw actuation about the axis. The actuation element features an external thread at least on one section. A switch element arranged on the base body is rotatable about the axis and has a passage, through which the actuation element extends. A spring arm arranged at the base body has an inner surface thread engagement structure facing the external thread. The passage features in inner surface having an inner radius varying at least in sections in a circumferential direction. A spring arm outer surface contacts the switch element inner surface. Switch element rotation generates spring arm elastic deformation towards/away from the axis, whereby the thread engagement structure is selectively engaged or disengaged.

14 Claims, 7 Drawing Sheets

(56) References Cited

U.S. PATENT DOCUMENTS

| | | |
|---|---|---|
| 8,105,332 B2 | 1/2012 | Downer |
| 9,326,848 B2 | 5/2016 | Woods |
| 10,350,059 B2 * | 7/2019 | Deacon ................ A61F 2/1664 |
| 2009/0112223 A1 * | 4/2009 | Downer ................ A61F 2/1667 |
| | | 606/107 |
| 2016/0128752 A1 | 5/2016 | Greter |

FOREIGN PATENT DOCUMENTS

| | | |
|---|---|---|
| EP | 3476375 A1 | 5/2019 |
| WO | 2019195951 A1 | 10/2019 |

* cited by examiner

INJECTOR FOR INTRAOCULAR LENSES

CROSS-REFERENCE TO RELATED APPLICATIONS

This application is the U.S. National Stage of PCT/EP2020/074761 filed on Sep. 4, 2020, the entire content is incorporated herein by reference in its entirety.

FIELD OF THE INVENTION

The invention relates to an injector for implantation of an intraocular lens, having a base body and an elongated actuation element, which projects at least partly into a rear section of the base body and which is movably guided in an actuation axis, and wherein a movement of the actuation element into the base body can be generated selectively by means of a push actuation along the actuation axis or by means of a screw actuation about the actuation axis, and wherein the actuation element has an external thread at least on one section, wherein a switch element, which can be rotated about the actuation axis, is arranged on the base body and has a passage, through which the actuation element extends.

BACKGROUND OF THE INVENTION

Injectors for the implantation of intraocular lenses into a human eye are well known. For this purpose, an intraocular lens can either be inserted into the injector via a lens cartridge with an intraocular lens inserted into it shortly before the lens is inserted into the eye, in order to expel the intraocular lens from an anterior ejection nozzle into the posterior chamber of the eye after subsequent injection of a viscoelastic medium. The ejection nozzle forms the open end of a lens guide section of the injector, which is located at the front of the base body.

In the base body, a piston is movably guided along the actuation axis, and the piston, which is connected to the actuation element successive to each other along the actuation axis, can come into contact with the intraocular lens and expel it through the ejection nozzle when the actuation element is advanced and thus transferred to the piston in the direction of the ejection nozzle.

In order to move the piston in a controlled manner within the base body of the injector and, advancing further in the direction of the ejection nozzle, also through the lens guide section, the actuation element is provided, which projects into the base body in such a way that, when the actuation element is advanced in the actuation axis, the piston first contacts the intraocular lens and can then be moved together with the intraocular lens in the direction of the ejection nozzle until the intraocular lens is ejected into the posterior eye chamber. Injectors of the newer type are used as disposable injectors and are disposed of after single use and after ejection of a pre-loaded intraocular lens loaded into the injector. This type of injectors is generally referred to as pre-load system.

Advancing the actuation element into a rear opening in the base body is usually done manually by the operator, i.e. the ophthalmologist. Injectors are known, which in a first operating mode enable a pure pushing movement, which pushing movement is manually introduced into the actuation element, and, in a second operating mode, a rotary movement is enabled, which is introduced into the same actuation element in order to move the actuation element along the actuation axis in the same way. In this respect, injectors of newer design are capable of both push and screw actuation, for which purpose a corresponding device for switching the operating mode is provided on the injector.

For example, EP 3 476 375 A1 reveals an injector for the implantation of an intraocular lens, and an actuation element can be driven into the base body either by a push or by a screw movement, wherein the screw movement can be manually introduced into a rotating element, which has a direct threaded connection with an external thread of the actuation element. If, however, the actuation element is manually pushed into the base body, in the rotating element is caused a free rotating movement. If the rotating element is driven into the base body either by pushing on the back of the actuation element or by manually turning the rotating element, the actuation element can drive the intraocular lens in contact with the piston out of the ejection nozzle at the front end.

The WO 2019/195951 A1 reveals another design of an injector for the implantation of an intraocular lens into a human eye, having a base body into which an elongated actuation element projects in sections at the rear and is movably guided in an actuation axis, and wherein a movement of the actuation element into the base body can be produced optionally by means of a push actuation of the actuation element along the actuation axis or by means of a screw actuation of the actuation element about the actuation axis, for which purpose the actuation element has an external thread at least on one section. In order to switch over between the push actuation and the screw actuation of the actuation element, two opposite folding and unfolding wing handles are provided, wherein the unfolded position allows the operating mode to be switched to push actuation and in a folded position to screw actuation. In the operating mode of the push actuation the foldable wing handles can be used as finger grips, so that an operator can grip the injector at the wing handles between the index finger and the middle finger, in order to finally push the actuation element into the base body with the thumb at the back. Once the wing grips are folded, the actuation element can be screwed into the base body by holding the base body in a first hand of the operator and screwing the actuation element with the second hand of the operator.

Adjustment of the injector for either push or screw actuation is usually performed by an medical assistant, and then the ophthalmologist applies the injector in the preset mode by inserting the ejection nozzle at the anterior lens guide section into the eyeball and then actuating the actuation element until the intraocular lens is expelled into the posterior eye chamber.

SUMMARY OF THE INVENTION

The objective of the invention is the further development of an injector for the implantation of an intraocular lens into a human eye, wherein the injector should have the simplest possible switchability between the push actuation and the screw actuation of the actuation element for advancing the intraocular lens. In particular, it shall be possible to switch the operating mode between the push actuation and the screw actuation in such a way that the injector is otherwise to be used in the same way, but wherein the switchover between the push actuation and the screw actuation should be adjustable immediately before the injector is used.

This objective is solved starting from an injector according to the generic term disclosed herein in combination with the characterizing features. Advantageous embodiments of the invention are also disclosed.

The invention relates to the technical teaching at least one spring arm is arranged at the base body, wherein the spring arm has a thread engagement structure on an inner surface facing the external thread, wherein the passage of the switch element features at least one inner surface having an inner radius varying at least in sections in a circumferential direction, and wherein an outer surface of the spring arm is in contact with the inner surface of the switch element, so that upon a rotation of the switch element about the actuation axis, due to the varying inner radius at the circumferential position of the spring arm, an elastic deformation of the spring arm towards the actuation axis and away from the actuation axis can be generated, whereby the thread engagement structure can be selectively engaged or disengaged with the external thread.

The core idea of the invention is a switch element, which can be manually rotated between two actuation positions, and in a first actuation position the switch element causes the thread engagement structure on the spring arm to engage with the external thread of the actuation element for the screw actuation, and in a second actuation position the switch element releases the spring arm with the thread engagement structure from the external thread of the actuation element, so that the former is disengaged from the external thread of the actuation element, and the actuation element is finally freely displaceable for the push actuation.

Thus, if the switch element is rotated into the second actuation position, the spring arm or several spring arms, especially two spring arms opposite to each other, can spring outward elastically by themselves, so that the thread engagement structure releases the external thread of the actuation element.

Due to the inner surface with the circumferentially varying inner radius, the at least one spring arm is pressed radially inwards when the switch element is turned into the first actuation position, so that the thread engagement structure engages with the external thread. For this purpose, the outer surface of the spring arm, in particular on the rear side of the internal thread engagement structure, is in contact with the inner surface of the switch element, and the inner surface "contracts" to some extent when the switch element is rotated, so that the spring arm or springs arms are pressed inwards and spring back outwards when the switch element is rotated in the opposite direction. The spring arms are fixed in the circumferential position on the base body and do not rotate with the rotation of the switch element.

This means that the switch element is formed without a thread. In this way, the injector can be switched over between the operating mode of push actuation and screw actuation with a simple switch element in the form of a rotary swivel or a slewing ring, without having to displace or to fold over an element on the outside of the injector. The switch element can be labeled, for example with "Push" and "Screw", and arrows can be applied to the switch element, so that the user can easily see in which direction the switch element must be rotated about the actuation axis in order to activate either the push or screw actuation.

The contact between the spring arm and the actuation element does not have to be a direct contact within the scope of an embodiment according to the invention, and it may also be provided, for example, that an eccentric element, in particular with an eccentric inner part, is arranged between the switch element and the spring arm in order to achieve the same effect in the sense of the invention, or the switch element consists of several components. In this case, an eccentric element can also induce a changing or varying inner radius with respect to rotatability about the actuation axis, to which the at least one spring arm is in contact, so that the same effect is achieved compared to the switch element, on whose inner surface the circumferentially varying inner radius is formed.

With particular advantage, the base body features a receiving section with a passage, through which the actuation element extends and onto which the switch element is rotatably received. The receiving section can be designed in a single piece with the base body or the receiving section can be attached to the base body, for example it can be clipped to it.

It is also advantageous if the at least one spring arm is arranged on the rear side of the receiving section or within the receiving section or on the base body. The spring arm can, for example, have a section running through the hollow receiving section and protrudes out of an open end at the rear of the receiving section. In this way, a section of the inner surface of the switch element can easily be brought into contact with the outer surface of the spring arm, while another section of the inner surface is designed with a constant inner radius over the circumference, with which the switch element is rotatably mounted on the receiving section.

With further advantage the switch element is snapped onto the receiving section and/or is guided rotatably on the receiving section in a certain axial position with respect to the actuation axis. The switch element can be snapped onto the receiving section during the manufacturing process, so that the switch element with a ring-shaped design is rotatably guided in a fixed axial position on the receiving section about the actuation axis. The switch element can be arranged on the receiving section in such a way that it can not be manually removed from the receiving section. For example, the outer circumference of the receiving section can be provided with detent means that allow the switch element to be moved in an assembly direction only and retain the switch element in an opposite detaching direction.

In addition, detent positions can be provided for the switch element in the circumferential direction, which are designed in such a way that the user experiences a haptic feedback, for example by having to overcome a resistance before the detent position, and so that the switch element can lock in each the detent position for pushing operation and the detent position for screwing operation, for example in the rotary end positions of the switch element in its arrangement on the receiving section.

With further advantage, the base body features a wing handle, wherein the receiving section adjoins the rear side of the wing handle as an extension. If the operator uses the injector either in push mode or in screw mode, the switch element does not interfere with the handling of the injector, because it is located behind the wing handle. While the actuation element is driven into the base body from the rear either by a push movement or by a screw movement, the user cannot obstruct the switch element, especially not inadvertently.

Finally, it is advantageous that at least one groove is provided in the outer circumference of the receiving section, and wherein at least one pin is formed on the inner surface of the switch element, and thus the pin can be guided in the groove. The groove is formed in particular in at least on one section in the circumferential direction of the outer surface of the receiving section over a partial circumference, wherein also two grooves may be applied with respectively associated pins on the inner side of the switch element, so that the switch element is applied to the receiving section without tilting. In particular, more than one pin can be assigned to each groove. It is also advantageous if the switch element features an inner circumferential section with a certain axial width, which is guided on the outer surface of the receiving section, so that a tilt free, minimal play and haptically high-quality rotating movement of the switch element is achieved.

The groove can run along at least on one section in the circumferential direction of the outer surface of the receiving section. In order to mount the switch element onto the receiving section, a further groove can be provided, which runs parallel to the actuation axis and merges into the circumferential groove. The groove or the grooves are provided for each pin on the inner side of the switch element, which facilitates mounting the switch element. The transition of the axially running groove into the circumferential groove can have a latching threshold over which the pin must be pushed and so that the switch element can finally be mounted on the receiving section in a captivated manner.

The circumferentially varying inner radius on the inner surface of the switch element can be designed as a single section or as a multiple section. In particular, one or more circumferential segments can be provided so that the inner surface with the circumferentially varying inner radius is formed on a circumferential segment of the switch element. In particular, several circumferential segments can also be provided evenly distributed over the entire circumference, for example two circumferential segments are provided opposite to each other with varying inner radii.

The changing or varying inner radius of the inner surface creates a distance of the inner surface to the actuation axis that is smaller or larger depending on the rotating position of the switch element, and if the switch element is rotated on the receiving section, the inner surface contracts at a certain circumferential position where the spring arm is located, and expands again in the opposite direction of rotation, thus allowing the spring arm(s) to move inwards and self-elastically outwards again, finally allowing the thread engagement structure to engage and disengage with the external thread on the actuation element.

In the axial direction of the switch element, i.e. in the direction of an axis of rotation or of its symmetry, in which the switch element can be rotated on the base body, the inner radius can of course remain constant for a discrete circumferential position. This results in particular in a line contact between the inner surface and the outer surface of the spring arm, wherein the outer surface of the spring arm can also be curved in such a way that it is adapted to the curved inner surface with the varying inner radius, so that finally also a surface contact can result between the outer surface of the spring arm and the inner surface with the inner radius tapering inwards of the switch element.

The circumferential segment can extend on a circumference with a circumferential angle of 360° or with a circumferential angle of 180° or with a circumferential angle of 120° or with a circumferential angle of 90°. Thus, for example, only one spring arm can be in contact with the inner surface if the circumferential angle extends over the full circle; and when a circumferential angle of 180° of the circumferential segment are provided, two opposing inner surfaces are provided, to which two spring arms are thus associated, and if the circumferential angle of the circumferential segment is 120°, three circumferential segments are provided, to which three spring arms are associated, and at a circumferential angle of 90° of each circumferential segment, four circumferential segments can be provided, to which four spring arms are associated, and so on.

In particular and preferably, two mutually opposite circumferential segments are formed in the inner surface of the switch element, and wherein two mutually opposite spring arms are arranged on the base body and/or on the receiving section, wherein the spring arms are each assigned to a circumferential segment and interact with the latter. If the injector is switched between the push actuation and the screw actuation, the switch element can be rotated to almost 180°, wherein the width of the spring arm must be taken into account so that no full 1800 results as a rotation angle. In this respect, the rotation angle for switching between the operating modes of the injector is regularly less than the circumferential extension of the circumferential segments with the associated circumferential angles.

Furthermore, it is an advantage if the external thread on the actuation element has a thread pitch of 3 mm to 20 mm or of 5 mm to 15 mm or of 9 mm to 11 mm. In particular, it is advantageous if the external thread on the actuation element has a thread pitch of 10 mm, so that the operator has to introduce an appropriate number of rotations into the actuation element during screw actuation in order to expel the intraocular lens advantageously, in particular to avoid having to perform too many turns and not too less turns, since with the latter a fine dosability of the ejection movement of the lens from the ejection nozzle would be lost.

The injector advantageously may feature a receiving means for a lens cartridge, in which an intraocular lens is inserted, and wherein the lens cartridge can be inserted into the receiving means. Such injectors may be offered independently of the intraocular lens specification, but in preparation for the use of the injector, the lens cartridge containing the intraocular lens with the required specification for the patient must be inserted. Then a viscoelastic medium gets injected so that the intraocular lens and also the inner lumen in the lens cartridge as well as the interior of the lens guide section are wetted and are at least partly filled with viscoelastic means. Finally, the lens can be expelled, with the injector being reusable or preferably intended for its single use as a disposable.

Accordingly, the injector can be designed as a so-called pre-load system, according to which the base body or the lens guide section features a receiving chamber, in which an intraocular lens is inserted, so that the injector forms an individually manageable and tradable unit with the intraocular lens already inserted. Accordingly, the lens guide section can also feature the receiving chamber, which then can also be understood as part of the base body. In this respect, the receiving chamber does not have to be arranged locally in the base body, but it can also be arranged in the lens guide section or between the lens guide section and the base body.

Moreover, a piston is received in the base body and can be displaced axially by the actuation element via a rotary joint in between. In particular, if the injector is to be operated by said screw actuation, the rotary movement of the actuation element must be decoupled from a movement of the piston, which in particular is only intended to perform a linear movement along the actuation axis without performing a rotary movement itself.

The base body can be formed in one piece with the receiving section and with the wing handle from a plastic body, wherein a lens guide section with a tip-side ejection nozzle for ejecting the intraocular lens is arranged at the front end of the base body.

BRIEF DESCRIPTION OF THE DRAWINGS

Further measures to improve the invention are described in more detail below, together with a description of a preferred embodiment of the invention shown in the Figures. It is shown in.

DETAILED DESCRIPTION OF THE INVENTION

Figure 1:
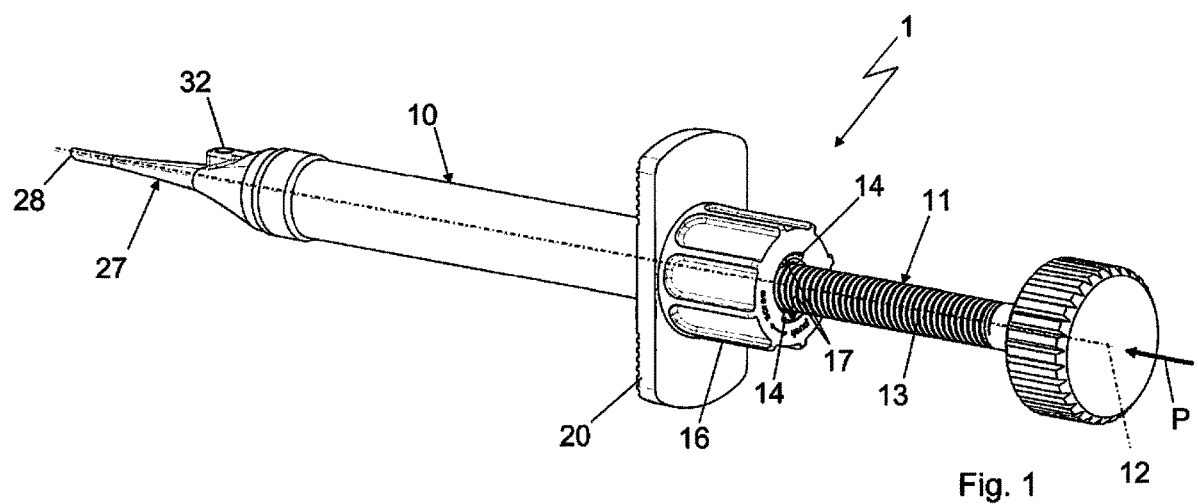
FIG. 1 a perspective view of an injector for implantation of an intraocular lens into a human eye, wherein the switch element of the injector is arranged in a position, in which the injector can be operated by a push actuation.
Figure 2:
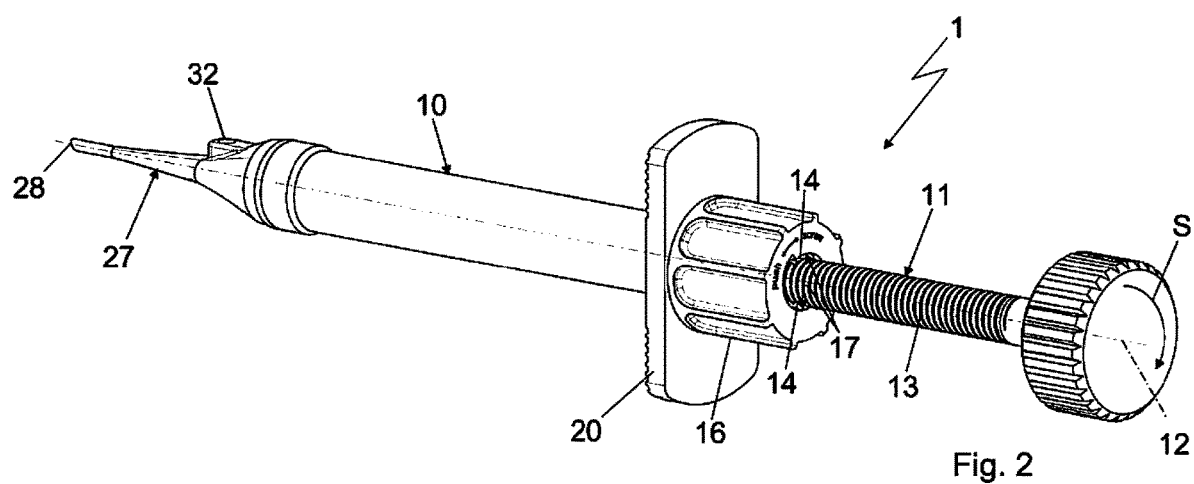
FIG. 2 a view of the injector as shown in FIG. 1, wherein the switch element of the injector is arranged in a position, in which the injector can be operated by a screw actuation.

FIGS. 1 and 2 show a perspective view of the injector 1, which can be used to implant an intraocular lens into a human eye. The injector 1 features a base body 10 as its main structural component, and an elongated actuation element 11 with a handle 31 at the rear end is partially inserted into the base body 10. The actuation element 11 has a section with an external thread 13 over its essential length, and the actuation element 11 is partially inserted into the rear end of the base body 10 in such a way that the handle 31 is formed at a free end of the actuation element 11.

At the front side of the base body 10, a lens guide section 27 is arranged in which the intraocular lens is inserted in a manner not shown closer. The main component of the base body 10 is approximately cylindrically or ergonomically designed for handling by a human hand and has an elongated extension, and the injector 1 with the base body 10, with the lens guide section 27 at the front end and with the actuation element 11 inserted in the rear end extends longitudinally in an actuation axis 12. The actuation axis 12 also forms the axis of rotation for the rotatable actuation element 11 with the handle 31 at the end.

For improved handling there is a wing handle 20 on the rear part of the base body 10, so that the injector 1 can be grabbed between the index finger and the middle finger with the wing handle 20, while the thumb can be used to push on the handle 31 on the rear side. At the back side of the wing handle 20 follows a switch element 16, which is mounted to the base body 10 so that it can rotate about the actuation axis 12, and the switch element 16 has a passage through which the actuation element 11 extends. The switch element 16 is arranged on the base body 10 in such a way that it has no direct contact with the actuation element 11 and does not directly interact with it.

On the lens guide section 27, a load opening 32 is shown through which a viscoelastic medium can be inserted before the injector 1 is operated. The viscoelastic medium then wets the inserted intraocular lens and the inner lumen, especially in the lens guide section 27, in order to promote the process of expelling the intraocular lens or to enable the intraocular lens to be expelled without damage.

The switch element 16 of the injector 1 forms a means to switch the operation mode of the injector 1 between a push actuation P and a screw actuation S. FIG. 1 shows a position of the switch element 16, which allows a push actuation P, while FIG. 2 shows the switch element 16 in a rotated position, which allows a screw actuation S.

In order to form a means of switching the mode between the push actuation P and the screw actuation S, the switch element 16 has an inner surface 17 on the inside, which varies its radius over the circumferential course of the switch element 16 in the manner of an Archimedean spiral at least in sections, in such a way that, during a rotation, the internal spring arms 14, which are arranged in a fixed position on the base body 10, can be moved towards the external thread 13 of the actuation element 11 where the switch element 16 tapers, and can be moved away from the external thread 13 when the switch element 16 widens in the opposite direction and reverses the tapering effect.

FIG. 1 shows a setting position of the switch element 16, according to which the spring arms 14 are located in a peripheral area on the inner surface 17 of the switch element 16, in which the spring arms 14 can spring open automatically, so that the distance to the actuation axis 12 increases and so that the spring arms 14 release the external thread 13 on the actuation element 11.

On the other hand, FIG. 2 shows the switch element 16 in a rotated position, according to which the spring arms 14 are pressed by the smaller inner radius at this point into the external thread 13 of the actuation element 11 and engage in it, so that in this position the screw actuation S for travelling the actuation element 11 into the body 10 is possible.

The further the actuation element 11 is pushed or screwed into the base body 10, the further the intraocular lens is moved forward in the direction of a front side ejection nozzle 28 at the lens guide section 27. A more detailed illustration of the function for switching the injector 1 between the push actuation P and the screw actuation S is shown in FIG. 3 in an exploded view of injector 1.

Figure 3:
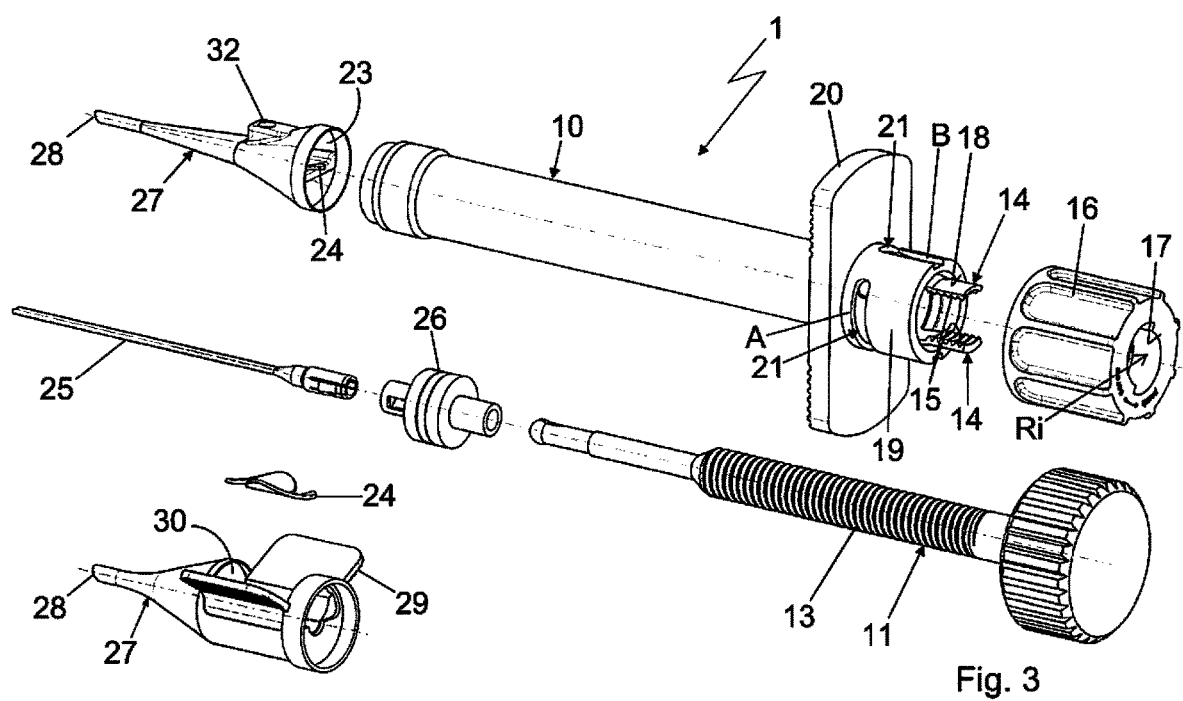
FIG. 3 an exploded view of the main components of the injector.

FIG. 3 shows the injector 1 in an exploded view, in which the essential parts of the injector 1 are shown, whereby further parts of the injector 1 are present, which are not shown, as they are not necessary for the presentation of the present invention, but which are also supposed to be part of the injector 1 according to the invention, so that the illustration is not to be understood conclusively.

The illustration in FIG. 3 shows the base body 10 separated from the lens guide section 27, and a lens guide section 27, which is shown in alignment with the actuation axis 12, is designed with a receiving chamber 23, in which an intraocular lens 24 is inserted (visible with a haptic on one side), and another lens guide section 27 is shown below which forms an alternative design and has a receiving means 30 for receiving a lens cartridge 29, in which the individually shown intraocular lens 24 is inserted. Once the lens cartridge 29 is inserted into the receiving means 30, the intraocular lens 24 can be expelled out of the front of the ejection nozzle 28 by a piston 25 into the posterior chamber of the human eye.

For this purpose, the piston 25 performs a linear movement in the actuation axis 12, and if the actuation element 11 is screwed into the base body 10 with a screw actuation, a rotary joint 26 is used to ensure that the rotational movement of the actuation element 11 is not transmitted into the piston 25.

Behind the wing handle 20, the base body 10 features said receiving section 19, onto which the switch element 16 is snapped, and it can be rotated about the actuation axis 12. For this purpose, the outer surface of the receiving section 19 features a groove 21, which runs in the circumferential direction in the shown section A, so that the switch element 16 can be rotated in an axially defined certain position about the actuation axis 12. A section B of the groove 21 is used for sliding on said switch element 16, wherein a kind of a detent is performed, which cannot be overcome itself by the switch element 16, so that the switch element 16 is inhibited to leave the section A and pass into section B of the groove 21 of the receiving section 19.

The receiving section 19 is sleeve-shaped and, in particular, is attached in one piece to the base body 10 at the back of the wing handle 20 and thus forming a section of the base body 10. Inside the receiving section 19, two spring arms 14 are arranged in an exemplary manner, wherein the spring arms 14 are rooted either on the inner surface of the receiving section 19 or on the back of the base body 10 or on the wing handle 20, respectively. Thus, the spring arms 14 can be moved resiliently inwards by elastic deformation towards the actuation axis 12 or outwards away from the actuation axis 12. In a non-activated arrangement of the spring arms 14, they feature a sufficient distance to each other, according to which the external thread 13 on the actuation element 11 can be moved freely and centrally between the two spring arms 14. In the commercial delivery condition of the injector 1, the switch element 16 therefore should be set in a position allowing for push actuation in order to non-stress the spring arms 14.

If the switch element 16 is snapped onto the receiving section 19, the switch element 16 can be rotated on the receiving section 19 in such a way that different circumferential positions of the inner surface 17 with a varying inner radius Ri come into contact with the outer surface 18 of the spring arms 14. As the inner radius Ri of the inner surface 17 changes along the continuous circumference, i.e. the inner radius Ri tapers or contracts inwardly, the spring arms 14 can either be pressed radially inward or automatically spring back outwards due to their intrinsic elasticity. Thus, depending on the position of the switch element 16 about the actuation axis 12, it is possible to adjust whether a thread engagement structure 15 on the inside of the spring arms 14 engages with the external thread 13 or whether the thread engagement structure 15 is disengaged from the external thread 13. If the thread engagement structure 15 on the spring arms 14 is in engagement with the external thread 13 on the actuation element 11, the injector 1 can be used by screw actuation S, and if the thread engagement structures 15 on the spring arms 14 are out of engagement with the external thread 13 on the actuation element 11, the injector 1 can be used by push actuation P.

Figure 4:
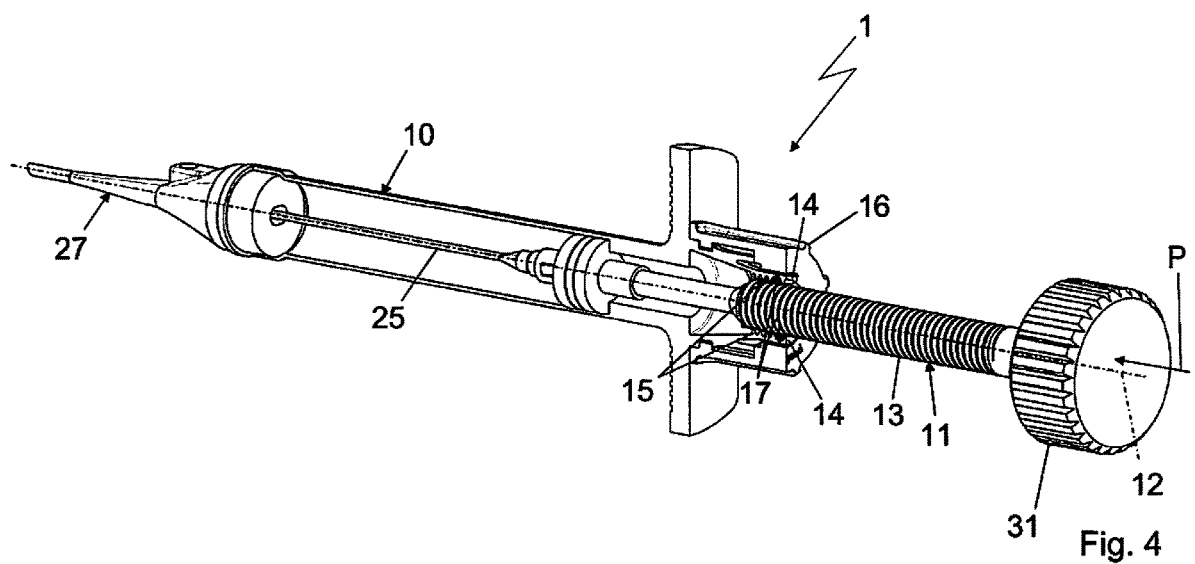
FIG. 4 a cross-sectional view of the injector in a perspective illustration, wherein the operating state of the injector is set up for push actuation.
Figure 5:
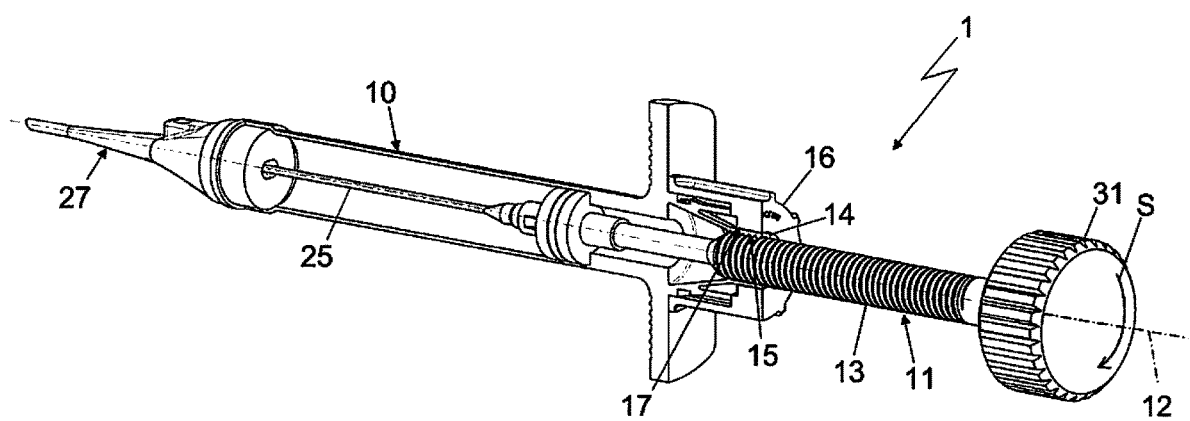
FIG. 5 the illustration of the injector as shown in FIG. 4, wherein the switch element has been rotated relative to the position shown in FIG. 4, so that the injector is set up for screw actuation.

FIGS. 4 and 5 show further perspective views of the injector 1 in a cross-section through the base body 10. For clarification, FIG. 4 shows the injector 1 in a state, in which it can be used by push actuation P, and FIG. 5 shows the injector 1 in a state, in which it can be used by screw actuation S.

If the injector 1 is to be provided in the operating mode of the push actuation P, the switch element 16 is rotated counterclockwise with respect to the viewing direction of the handle 31 until it is in the rotational position shown in FIG. 4. In this rotational position, the inner radius of the inner surface 17 in the contact position of the spring arm 14 is enlarged, so that the spring arm 14 relaxes and has a maximum distance to the actuation axis 12. In this position, the thread engagement structure 15 on the inside of the spring arm 14 does not engage with the external thread 13 of the actuation element 11. Accordingly, the actuation element 11 can be moved freely along the actuation axis 12 and the actuation element 11 can be pushed forward together with the piston 25 towards the lens guide section 27.

In FIG. 5, the switch element 16 is in a clockwise rotated position, according to which the inner radius of the inner surface 17 at the point of contact with the spring arm 14 is reduced to such an extent, that the thread engagement structure 15 is engaged with the external thread 13 on the actuation element 11. In this position of the switch element 16, the actuation element 11 can only be displaced in the actuation axis 12 if it is set in rotary motion by means of the handle 31 about the actuation axis 12 and finally screwed into the base body 10. The opposing thread engagement structures 15 of the spring arms 14 thus form a thread passage in the base body 10, through which the actuation element 11 can be screwed into the back of the base body 10. Only then the piston 25 can be moved forward in the direction of the lens guide section 27 and the intraocular lens can be expelled from the ejection nozzle.

Figure 6:
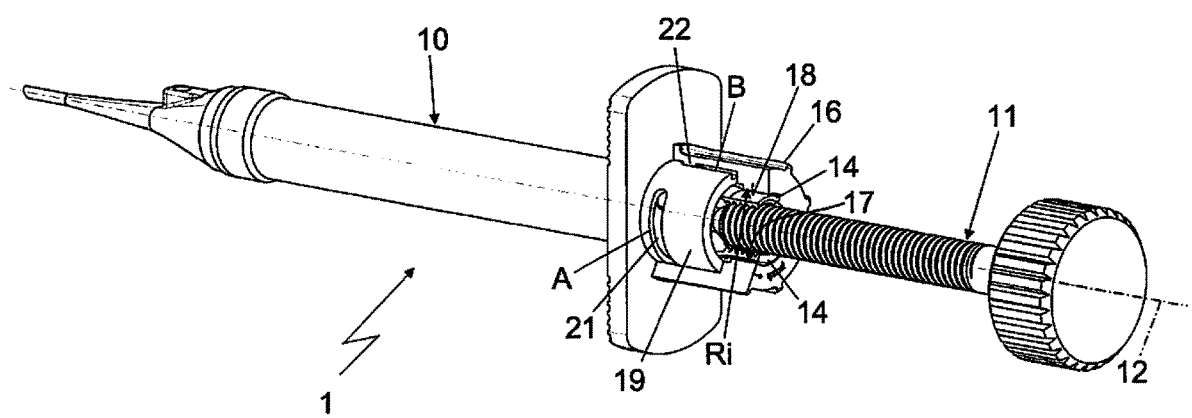
FIG. 6 a perspective view of the injector with a partially cross-sectional view of the switch element.

FIG. 6 shows another perspective view of the injector 1 with a partially cut switch element 16, which is snapped onto the receiving section 19. Inside the switch element 16, there are pins 22, one of which is visible by means of the cut and which runs in the grooves 21. Thereby, the switch element 16 can first be placed on the receiving section 19 via section B of the groove 21 and then be rotated about the actuation axis 12 within section A of the groove 21.

The spring arms 14 are designed with outer surfaces 18 on the rear side in such a way that they can slide along the inner surface 17 of the switch element 16, when the switch element 16 is rotated about the actuation axis 12. Since the spring arms 14 are rooted on the inside in the receiving section 19 or on the rear side of the base body 10, the spring arms 14 do not shift in their circumferential position about the actuation axis 12. Only in this way the outer surfaces 18 of the spring arms 14 come into contact with the inner surface 17 in different circumferential positions of the switch element 16, when the switch element 16 is rotated, so that the shifting of the spring arms 14 radially towards the actuation axis 12 and radially away from the actuation axis 12 can be produced by the varying inner radius Ri.

Figure 7:
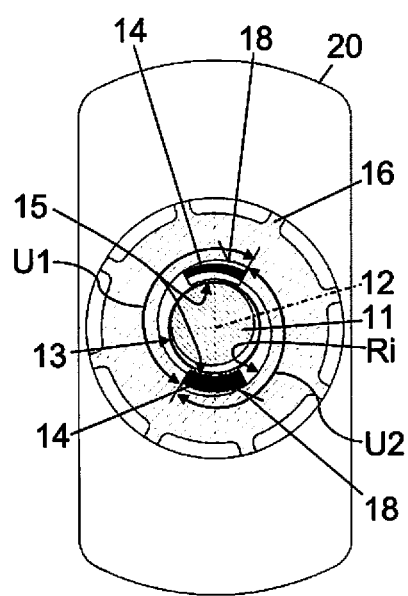
FIGS. 7 and 8 a cross-sectional view through the arrangement of the switch element on the base body with a push actuation (FIG. 7) and with a screw actuation (FIG. 8).
Figure 8:
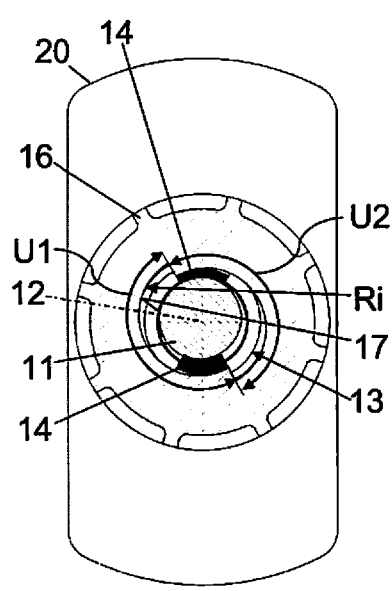

FIGS. 7 and 8 show a cross-sectional view through the arrangement of the switch element 16 in arrangement on the main body, represented by the wing handle 20. The actuation element 11 extends through the switch element 16, and the actuation axis 12 is perpendicular to the plane of the figures.

FIG. 7 shows the position of the switch element 16, in which the push actuation is enabled, and FIG. 8 shows a position of the switch element 16, in which the screw actuation is enabled.

To set the push actuation, the spring arms 14 are in contact with the inner surface 17 via their outer surfaces 18 at a circumferential position where the inner radius Ri is particularly large. The elastic springing of the spring arms 14 causes the thread engagement structure 15 to disengage from the external thread 13 on the actuation element 11.

As shown in FIG. 8, the switch element 16 can be rotated clockwise to a setting position, which allows screw actuation. In this position the outer surface 18 of the spring arm 14 is in contact with the inner surface 17 at a circumferential position where the inner radius Ri is smaller and the thread engagement structure 15 inside the spring arms 14 is brought into engagement with the external thread 13 on the actuation element 11. In this position, the actuation element 11 can only be screwed into the base body by a screwing movement.

The invention is not limited in its entirety to the preferred embodiment given above. Rather, a number of variants are conceivable which make use of the solution presented even if the design is fundamentally different. All features and/or advantages arising from the claims, the description or the figures, including constructional details or spatial arrangements, may be essential to the invention, both individually and in various combinations.

REFERENCE NUMBERS 1 injector
10 base body
11 actuation element
12 actuation axis
13 external thread
14 spring arm
15 thread engagement structure
16 switch element
17 inner surface
18 outer surface
19 receiving section
20 wing handle
21 groove
22 pin
23 receiving chamber
24 intraocular lens
25 piston
26 rotary joint
27 lens guide section
28 ejection nozzle
29 lens cartridge
30 receiving means
31 handle
32 load opening
A groove section
B groove section
Ri inner radius
P push actuation
S screw actuation
U1 circumferential segment
U2 circumferential segment

The invention claimed is:

1. An injector for implantation of an intraocular lens, comprising:
a base body;
an elongated actuation element which projects at least partly into a rear section of the base body and which is movably guided along an actuation axis, wherein a movement of the actuation element into the base body is generated selectively by a push actuation along the actuation axis or by a screw actuation about the actuation axis, and wherein the actuation element features an external thread at least on one section; and
a switch element, which can be rotated about the actuation axis, arranged on the base body and having a passage, the actuation element extending through the passage; wherein;
at least one spring arm is arranged at the base body, the spring arm having a thread engagement structure on an inner surface facing the external thread;
the passage of the switch element features at least one inner surface having an inner radius varying at least in sections in a circumferential direction; and
an outer surface of the spring arm is in contact with the inner surface of the switch element, so that upon a rotation of the switch element about the actuation axis, due to the varying inner radius at the circumferential position of the spring arm, an elastic deformation of the spring arm towards the actuation axis and away from the actuation axis is generated, whereby the thread engagement structure is selectively engaged or disengaged with the external thread.

2. The injector according to claim 1, wherein:
the base body has a receiving section with a passage, through which the actuation element extends and onto which the switch element is rotatably received; and
the base body has a wing handle, the receiving section adjoining the rear side of the wing handle as an extension.

3. The injector according to claim 2, wherein:
the at least one groove is provided in an outer circumference of the receiving section; and
at least one pin is formed on an inside of the switch element, the pin being guided in the groove.

4. The injector according to claim 3, wherein:
the groove runs at least on one section in a circumferential direction of the outer surface of the receiving section.

5. The injector according to claim 2, wherein:
the base body is formed in one piece with the receiving section and with the wing handle from a plastic body; and
a lens guide section with a tip-side ejection nozzle for ejecting the intraocular lens is arranged at a front end of the base body.

6. The injector according to claim 1, wherein:
the at least one spring arm is arranged to the receiving section in a position at an end side or within the receiving section, and the arrangement is formed to the receiving section or to the base body.

7. The injector according to claim 1, wherein:
the switch element is snapped onto the receiving section and is guided rotatably on the receiving section in a certain axial position with respect to the actuation axis.

8. The injector according to claim 1, wherein:
the inner surface with the inner radius varying in the circumferential direction is formed on a circumferential segment of the switch element.

9. The injector according to claim 8, wherein:
the circumferential segment extends on a circumference with a circumferential angle of 360° or with a circumferential angle of 180° or with a circumferential angle of 120° or with a circumferential angle of 90°.

10. The injector according to claim 8, wherein:
the circumferential segment of the switch element comprises two opposite circumferential segments formed in the inner surface of the switch element; and
the at least one spring arm comprises two opposite spring arms arranged at the base body and/or at the receiving section, the spring arms each assigned to one of the circumferential segments and interact with the one of the circumferential segments.

11. The injector according to claim 1, wherein:
the external thread on the actuation element has a thread pitch of 3 mm to 20 mm or of 5 mm to 15 mm or of 9 mm to 11 mm.

12. The injector according to claim 1, wherein:
the injector features a receiving means for a lens cartridge, in which an intraocular lens is inserted, and the lens cartridge is insertable into the receiving means.

13. The injector according to claim 1, wherein:
the base body features a receiving chamber, in which an intraocular lens is inserted, so that the injector forms an individually manageable and tradable unit together with the inserted intraocular lens.

14. The injector according to claim 1, further comprising:
a piston received in the base body, the piston being displacable axially by the actuation element via a rotary joint.

\* \* \* \* \*